US007354450B2

(12) United States Patent
Bicek et al.

(10) Patent No.: US 7,354,450 B2
(45) Date of Patent: Apr. 8, 2008

(54) STENT WITH WISHBONE CONNECTORS AND SERPENTINE BANDS

(75) Inventors: Andrew D. Bicek, Big Lake, MN (US); Timothy S. Girton, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1074 days.

(21) Appl. No.: 10/058,640

(22) Filed: Jan. 30, 2002

(65) Prior Publication Data

US 2003/0144729 A1   Jul. 31, 2003

(51) Int. Cl.
*A61F 2/06* (2006.01)
(52) U.S. Cl. ..................................... 623/1.15
(58) Field of Classification Search ............... 623/1.15, 623/1.1
See application file for complete search history.

(56) References Cited

U.S. PATENT DOCUMENTS

| 5,091,205 | A | | 2/1992 | Fan ................................ 427/2 |
| 5,514,154 | A | | 5/1996 | Lau et al. .................... 606/195 |
| 5,843,120 | A | | 12/1998 | Israel et al. ................. 606/198 |
| 5,931,867 | A | | 8/1999 | Haindl .......................... 623/1 |
| 5,935,162 | A | | 8/1999 | Dang ............................ 623/1 |
| 5,964,798 | A | | 10/1999 | Imran ........................... 623/1 |
| 6,019,789 | A | * | 2/2000 | Dinh et al. ................ 623/1.15 |
| 6,171,334 | B1 | | 1/2001 | Cox .......................... 623/1.15 |
| 6,179,867 | B1 | | 1/2001 | Cox .......................... 623/1.15 |
| 6,190,405 | B1 | | 2/2001 | Culombo et al. ........... 623/1.15 |
| 6,273,911 | B1 | | 8/2001 | Cox et al. .................. 623/1.15 |
| 6,375,676 | B1 | | 4/2002 | Cox .......................... 623/1.16 |
| 2001/0016770 | A1 | | 8/2001 | Allen et al. ................ 623/1.15 |

FOREIGN PATENT DOCUMENTS

| WO | 96/26689 | 9/1996 |
| WO | 01/26584 | 4/2001 |

* cited by examiner

*Primary Examiner*—Corrine McDermott
*Assistant Examiner*—Christopher Daniel Prone
(74) *Attorney, Agent, or Firm*—Vidas, Arrett & Steinkraus, P.A.

(57) ABSTRACT

A stent comprises a plurality of axially spaced serpentine bands. Each serpentine band has a proximal and distal end and consists of a plurality of interconnected struts. The struts are of substantially the same length. Serpentine bands which are adjacent one another are connected one to the other. The stent further comprises a plurality of wishbone connectors. Each wishbone connector connects two serpentine bands which are adjacent one another. The wishbone connectors have an elongate portion which is disposed between the two serpentine bands and does not overlap longitudinally with either of the two serpentine bands. The elongate portion has a proximal end and a distal end. The proximal end has two legs extending therefrom to one of the two serpentine bands and the distal end has two legs extending therefrom to the other of the two serpentine bands. At least one wishbone connector connects serpentine bands which are adjacent one another.

20 Claims, 5 Drawing Sheets

STENT WITH WISHBONE CONNECTORS AND SERPENTINE BANDS

BACKGROUND OF THE INVENTION

Stents are placed or implanted within a blood vessel for treating stenoses, strictures or aneurysms therein. They are implanted to reinforce collapsing, partially occluded, weakened, or dilated sections of a blood vessel. They have also been implanted in other bodily vessels including arteries, veins, biliary ducts, urethras, fallopian tubes, bronchial tubes, the trachea and the esophagus.

Stents are typically either self-expanding or mechanically expandable via the application of radially outward force from within the stent, as by inflation of a balloon. Hybrid stents, e.g. stents which are both self-expanding and mechanically expandable are also known.

An example of a balloon expandable stent is shown in U.S. Pat. No. 5,843,120. An example of a self-expanding stent is described in WO 96/26689.

It is desirable to provide a stent which is both flexible and compression resistant. The conventional approach to increasing compression resistance involves increasing the thickness of the struts of the stent. This approach, however, results in a less flexible stent. Similarly, the conventional approach to increasing flexibility, namely by decreasing the thickness of the struts, results in a stent with less compression resistance. Achieving both increased flexibility and increased compression resistance remains a difficult problem. There remains a need for inventive stent designs which demonstrate increased flexibility and increased compression resistance.

All US patents, applications and all other published documents mentioned anywhere in this application are incorporated herein by reference in their entirety.

Without limiting the scope of the invention, a brief summary of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well for the purposes of complying with 37 C.F.R. 1.72.

BRIEF SUMMARY OF THE INVENTION

In one embodiment, the invention is directed to a stent having a proximal end and a distal end, and comprising a plurality of axially spaced serpentine bands. Each serpentine band has a proximal end and a distal end and consists of a plurality of interconnected struts. The struts are of substantially the same length. Serpentine bands which are adjacent one another are connected one to the other. The stent further comprises a plurality of wishbone connectors, each of which connects two serpentine bands which are adjacent one another. Each of the wishbone connectors have an elongate portion which is disposed between the two serpentine bands and does not overlap longitudinally with either of the two serpentine bands. The elongate portion of the wishbone connector has a proximal end and a distal end. The proximal end has two legs extending therefrom to one of the two serpentine bands and the distal end has two legs extending therefrom to the other of the two serpentine bands. At least one wishbone connector connects serpentine bands which are adjacent one another. Typically, at least two wishbone connectors extend between each two adjacent serpentine bands. Optionally, where each serpentine band comprises alternating peaks and troughs, the number of peaks in the stent will be twice the number of wishbone connectors.

Desirably, each serpentine band comprises a plurality of alternating peaks and troughs and each leg of each wishbone connector extends from a location on a serpentine band between a peak and a trough.

In accordance with the invention, the elongate portions of the connectors may extend in a direction non-parallel to the longitudinal axis of the stent. In one embodiment, the elongate portions of the connectors have a plurality of turns.

Also in accordance with the invention, the legs extending from the first end of the elongate portion of each wishbone connector may be circumferentially and longitudinally displaced from the legs extending from the second end of the elongate portion of the wishbone connector.

Desirably, each serpentine band comprises a plurality of alternating peaks and troughs and each leg of each wishbone connector extends from a location on a serpentine band between a peak and a trough.

Also desirably, the width of the serpentine bands exceeds the width of the wishbone connectors.

The invention is also directed to a stent having a first proximal end and a distal end and comprising a plurality of axially spaced serpentine bands. Each serpentine band has a proximal end, a distal and a plurality of peaks and troughs. All of the peaks of a serpentine are longitudinally aligned with one another and all of the troughs of a serpentine band are longitudinally aligned with one another. Serpentine bands which are adjacent one another are connected one to the other. The stent further comprises a plurality of wishbone connectors. Each wishbone connector connects two serpentine bands which are adjacent one another and has an elongate portion which is disposed between the two serpentine bands and does not overlap longitudinally with either of the two serpentine bands. The elongate portion has a proximal end and a distal end. The proximal end has two legs extending therefrom to one of the two serpentine bands and the distal end has two legs extending therefrom to the other of the two serpentine bands. At least one wishbone connector connects serpentine bands which are adjacent one another. Typically, at least two wishbone connectors extend between each two adjacent serpentine bands. Optionally, where each serpentine band comprises alternating peaks and troughs, the number of peaks in the stent may be twice the number of wishbone connectors.

Desirably, each serpentine band comprises a plurality of alternating peaks and troughs and each leg of each wishbone connector extends from a location on a serpentine band between a peak and a trough.

In accordance with the invention, the elongate portions of the connectors may optionally extend in a direction non-parallel to the longitudinal axis of the stent. Desirably, the elongate portions of the connectors have a plurality of turns. The legs extending from the first end of the elongate portion of each wishbone connector may optionally be circumferentially and longitudinally displaced from the legs extending from the second end of the elongate portion of the wishbone connector.

Each serpentine band may comprise a plurality of alternating peaks and troughs and each leg of each wishbone connector may extend from a location on a serpentine band between a peak and a trough.

The invention is also directed to a stent comprising a plurality of first and second alternating serpentine bands where the first serpentine bands are of one geometry and the second serpentine bands are of a geometry different than the first serpentine bands. Each of the first and second serpentine bands has a proximal end and a distal end. Each second serpentine band is connected to one proximally adjacent first serpentine band via a plurality of first connectors and to one distally adjacent first serpentine band via a plurality of second connectors. Each second serpentine band is characterized by a repeating pattern of two or more consecutive first connectors extending distally from the second serpentine band followed by two or more first connectors extending proximally from the second serpentine band.

In one embodiment, the first serpentine bands are comprised of a plurality of interconnected first struts and the second serpentine bands are comprised of a plurality of interconnected second struts. The second struts are narrower than the first struts. Typically, at least some of the second serpentine bands each comprise a plurality of openings of a first shape and a plurality of openings of a second shape, the second shape different from the first shape. Desirably, at least some of the second serpentine bands each comprise a plurality of openings some of which are non-parallel to the longitudinal axis of the second serpentine segment.

In a particularly desirable embodiment of the invention, the first and second connectors are substantially straight.

Additional details and/or embodiments of the invention are discussed below.

DETAILED DESCRIPTION OF THE INVENTION

Figure 2:
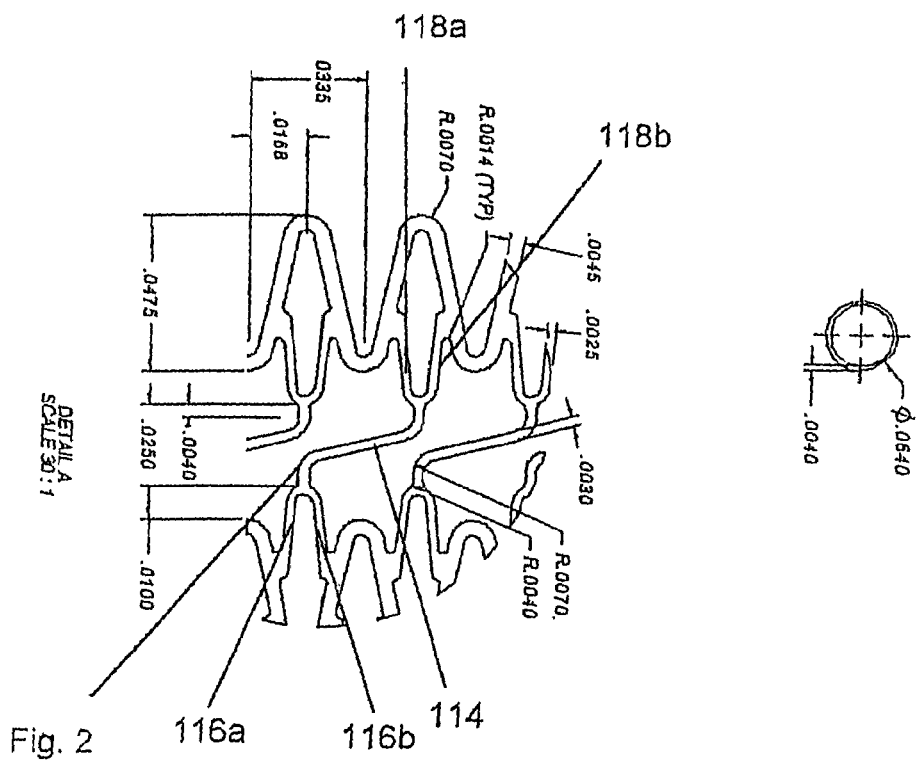
FIG. 2 is an expanded view of a portion 2 of the stent of FIG. 1.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1:
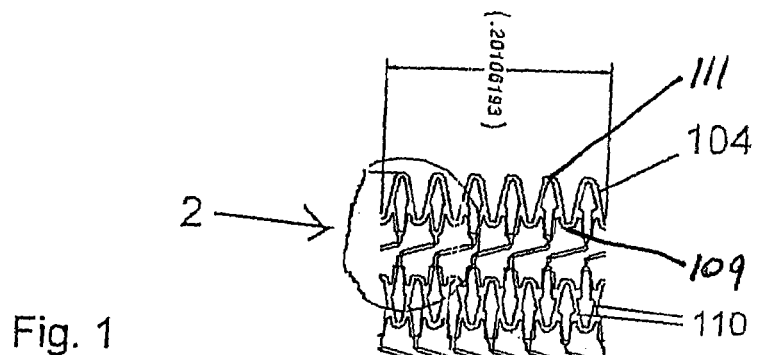
FIG. 1 is a view of an inventive stent in an unexpanded configuration in the flat.
Figure 1:
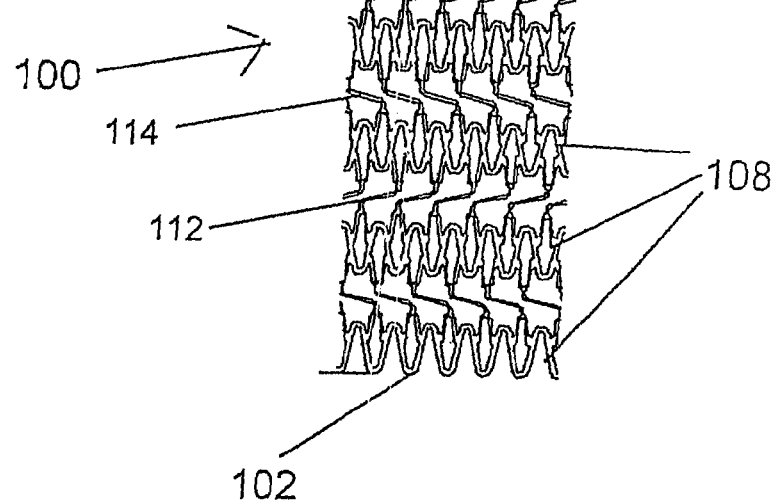

In one embodiment, as shown in FIG. 1, the invention is directed to a stent, shown generally at 100, having a proximal end 102 and a distal end 104, and comprising a plurality of axially spaced serpentine bands 108. Each serpentine band has a proximal end and a distal end and consists of a plurality of interconnected struts 110. The struts are of substantially the same length. Serpentine bands which are adjacent one another are connected one to the other. The stent further comprises a plurality of wishbone connectors 112 having elongate portions 114 which are disposed between adjacent serpentine bands 108 and do not overlap longitudinally with either of the two serpentine bands. Elongate portion 114 of wishbone connector 112 has a proximal end and a distal end. The proximal end has two legs 116a,b extending therefrom to one of the two serpentine bands and the distal end has two legs 118a,b extending therefrom to the other of the two serpentine bands. At least one wishbone connector connects serpentine bands which are adjacent one another. Typically, at least two wishbone connectors extend between each two adjacent serpentine bands. Optionally, where each serpentine band comprises alternating peaks and troughs, the number of peaks in the stent will be twice the number of wishbone connectors.

The invention is also directed to a stent such as that shown generally at 100 in FIG. 1 having a first proximal end 102 and a distal end 104 and comprising a plurality of axially spaced serpentine bands 108. Each serpentine band 108 has a proximal end, a distal end and a plurality of peaks 109 and troughs 111. As shown in FIG. 1, all of the peaks of a given serpentine are longitudinally aligned with one another and all of the troughs of a given serpentine band are longitudinally aligned with one another. Serpentine bands 108 which are adjacent one another are connected one to the other. The stent further comprises a plurality of wishbone connectors 112. Each wishbone connector 112 connects two serpentine bands 108 which are adjacent one another and has an elongate portion 114 which is disposed between the two serpentine bands and does not overlap longitudinally with either of the two serpentine bands. The elongate portion 114 has a proximal end and a distal end. The proximal end has two legs 116a,b extending therefrom to one of the two serpentine bands and the distal end has two legs 118a,b extending therefrom to the other of the two serpentine bands. At least one wishbone connector connects serpentine bands which are adjacent one another. Typically, at least two wishbone connectors extend between each two adjacent serpentine bands. Optionally, where each serpentine band comprises alternating peaks and troughs, the number of peaks in the stent will be twice the number of wishbone connectors.

Desirably, as shown in FIG. 1, each serpentine band of the above described stents comprises a plurality of alternating peaks and troughs and each leg of each wishbone connector extends from a location on a serpentine band between a peak and a trough. In other embodiments of the invention, the legs of the wishbone connector may extend from other portions along the serpentine bands—for example, from the peaks on one band and the troughs on an adjacent band.

In accordance with the invention, and as shown in FIG. 1, the elongate portions 114 of wishbone connectors 112 of the embodiments described above may include one or more portions which extend in a direction non-parallel to the longitudinal axis of the stent. In the embodiment of FIG. 1, the elongate portions of the connectors have two turns. In other embodiments of the invention, the elongate portions may be straight, without any turns, may have one turn or may have in excess of to turns. The elongate portion may be formed of a plurality of interconnected linear segments arranged at angles to one another or may be in the form of a one or more curved sections. Also in accordance with the invention, the legs extending from the first end of the elongate portion of each wishbone connector may be circumferentially and longitudinally displaced from the legs extending from the second end of the elongate portion of the wishbone connector.

In order to give the stent both flexibility and compression resistance, the wishbone connectors are desirably not as wide as the width of the serpentine bands, as shown in FIGS. 1 and 2. The stent may also be provided with wishbone connectors which are thinner than the thickness of serpentine bands. It is also within the scope of the invention to provide a stent with wishbone connectors which are both thinner and narrower than the serpentine bands.

Figure 3:
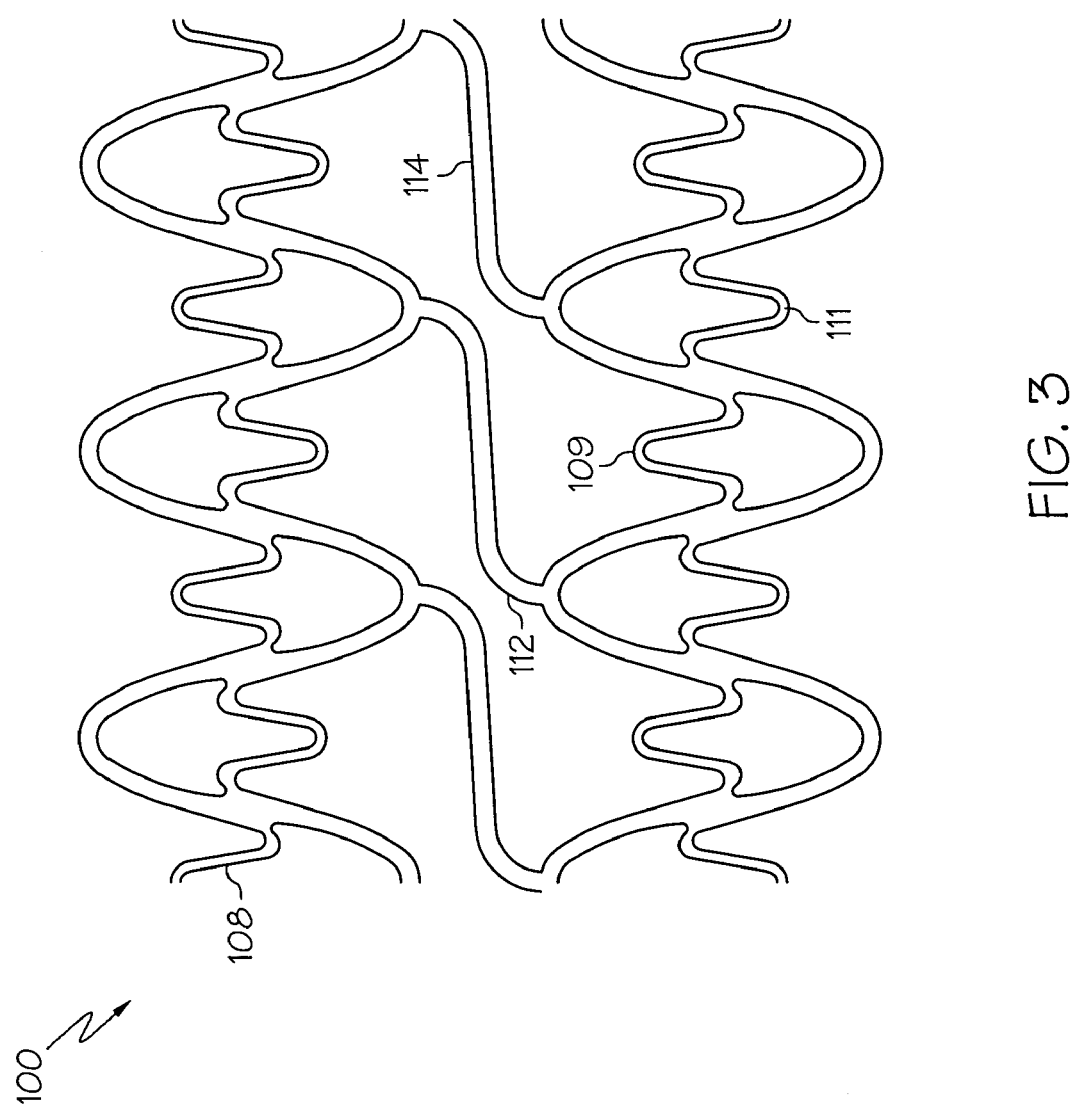
FIG. 3 is a view of an inventive stent in an unexpanded configuration in the flat.

Another embodiment of the invention is shown at 100 in FIG. 3. Stent 100 comprises a plurality of serpentine bands 108 which are interconnected by wishbone connectors 112. Wishbone connectors 112 include an elongated portion having a plurality of curves. Desirably, as shown in FIG. 3, the elongated portion includes two substantially longitudinally extending sections, one at each end of the elongate portion and a substantially circumferentially extending section in between the ends. As such, each wishbone connector connectors has ends which are longitudinally and circumferentially offset from one another. The peaks of each serpentine band are not all longitudinally aligned with every third peak extending in a distal direction relative to the other peaks. Similarly, the troughs of the serpentine band are not all longitudinally aligned. Rather, every third trough extends in a proximal direction relative to the other troughs. Also as shown in FIG. 3, the number of peaks in the proximal band of the stent exceeds the number of wishbone connectors in the stent. In the embodiment of FIG. 3, each wishbone connector has one end which straddles two peaks and one trough and another end which straddles two troughs and a peak. Other arrangements are also within the scope of the invention.

Figure 4:
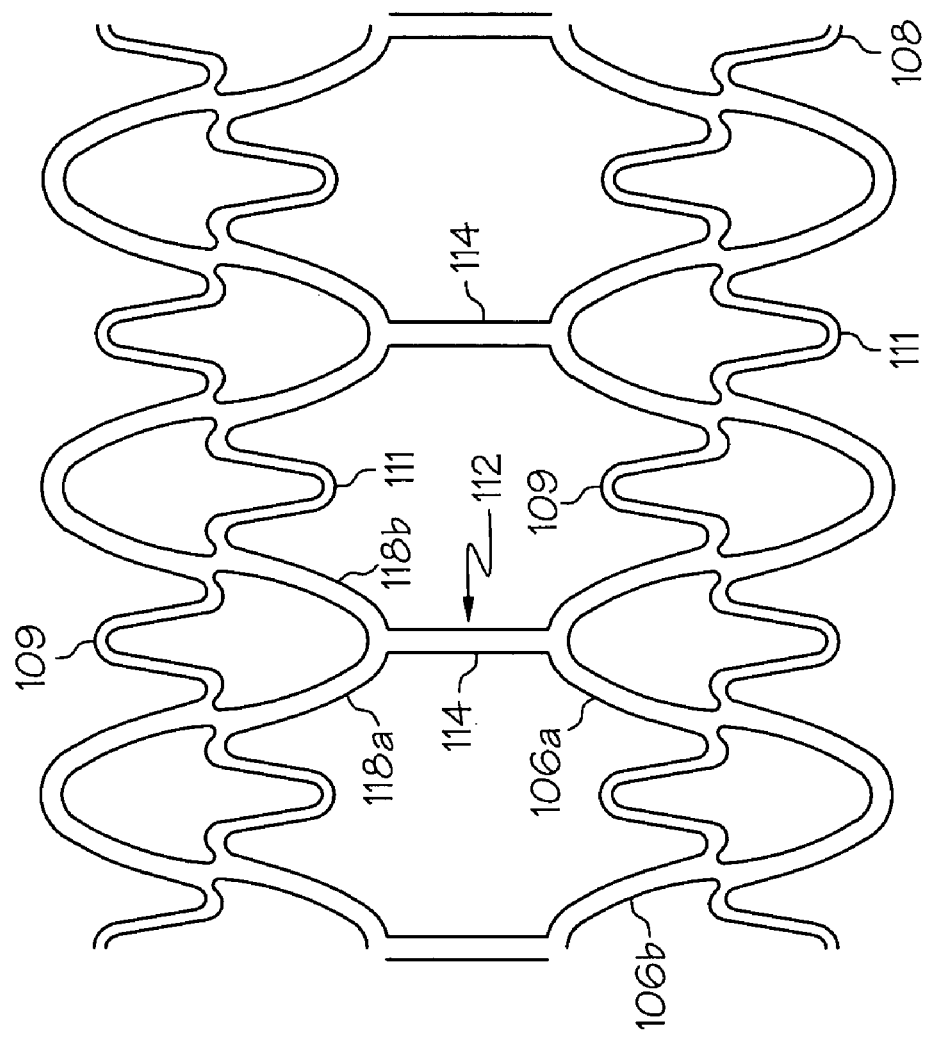
FIG. 4 is a view of an inventive stent in an unexpanded configuration in the flat.

Another embodiment of the invention is show at 100 in FIG. 4. Stent 100 comprises a plurality of serpentine bands 108 which are interconnected by wishbone connectors 112. The stent of FIG. 4 differs from that of FIG. 3 in several aspects. First, the elongate portions 114 of the wishbone connectors 112 are substantially longitudinal. Second, legs 116*a,b* and 118*a,b* of the wishbone connectors 112 intersect with the serpentine bands at a larger angle of intersection than those in the stent of FIG. 3. Additionally, the serpentine bands have a ripple between adjacent peaks and troughs. It is also within the scope of the invention to provide any of these features in any of the other stents disclosed herein.

Figure 5:
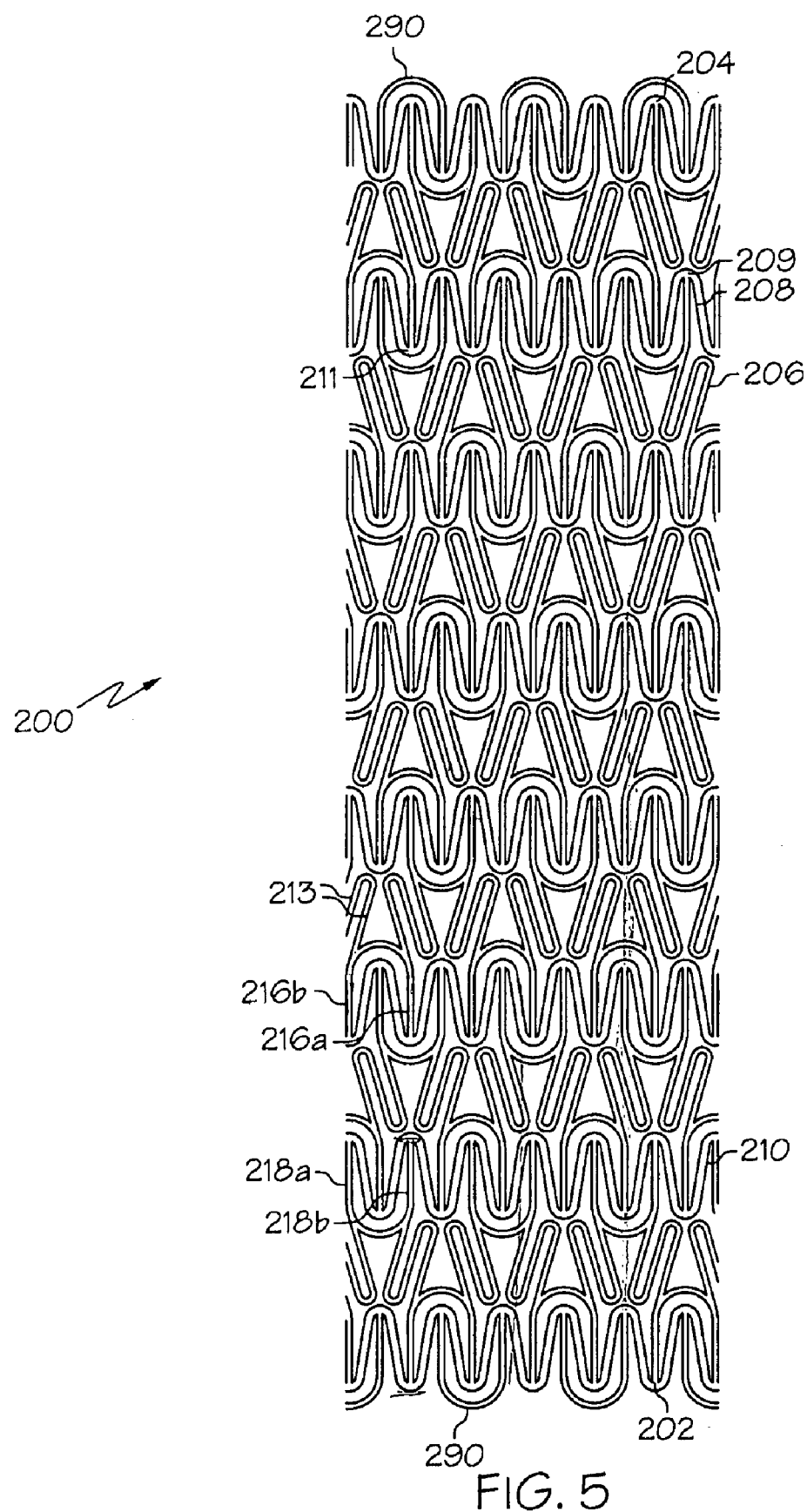
FIG. 5 is a view of an inventive stent in an unexpanded configuration in the flat.

The invention is also directed to a stent such as that shown generally at 200 in FIG. 5, having a proximal end 202 and a distal end 204 and comprising a plurality of first and second alternating serpentine bands 208 and 206 where the first serpentine bands 208 are of one geometry and the second serpentine bands 206 are of a geometry different than the first serpentine bands. Each of the first and second serpentine bands has a proximal end and a distal end. Each second serpentine band 206 is connected to one proximally adjacent first serpentine band 208 via a plurality of first connectors 216*a,b* and to one distally adjacent first serpentine band via a plurality of second connectors 218*a,b*. Each second serpentine band 206 is characterized by a repeating pattern of two or more consecutive first 216*a,b* connectors extending distally from the second serpentine band followed by two or more second connectors 218*a,b* extending proximally from the second serpentine band 206.

In the embodiment of FIG. 5, the first serpentine bands are comprised of a plurality of interconnected first struts 210 and the second serpentine bands are comprised of a plurality of interconnected second struts 213. Second struts 213 are narrower than first struts 210. Typically, at least some of the second serpentine bands each comprise a plurality of openings of a first shape and a plurality of openings of a second shape, the second shape different from the first shape. Desirably, at least some of the second serpentine bands each comprise a plurality of openings some of which are non-parallel to the longitudinal axis of the second serpentine segment.

In the embodiment of FIG. 5, it is also noted that the second serpentine band can be seen to comprise a plurality of circumferentially adjacent, interconnected wishbone connectors.

Figure 6:
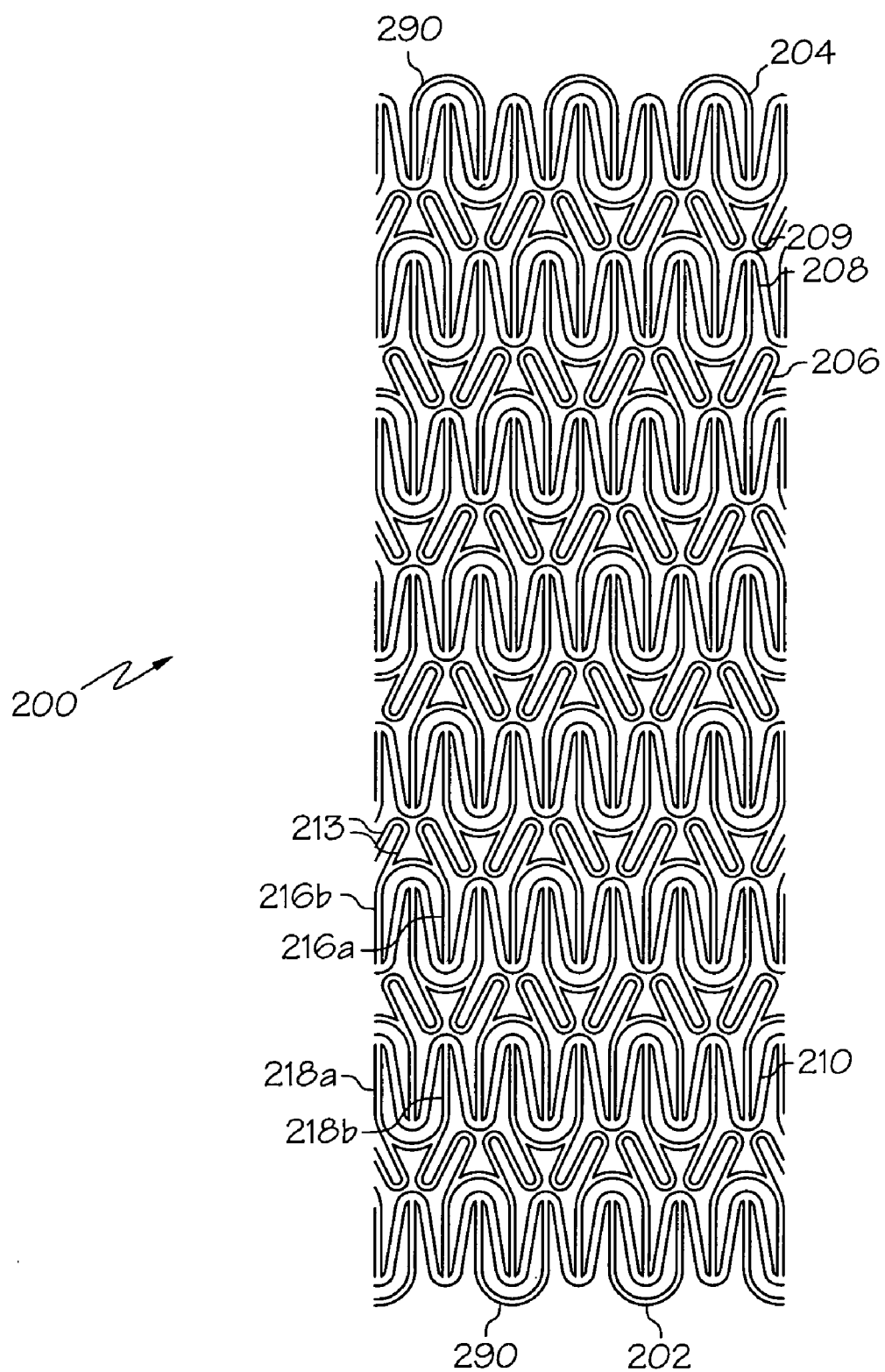
FIG. 6 is a view of an inventive stent in an unexpanded configuration in the flat.

The embodiment of FIG. 6 is similar to that of FIG. 5, differing in that the amplitude of the second serpentine band of FIG. 6 is smaller than that of FIG. 5.

In some embodiments, examples of which are shown in FIGS. 5 and 6, the serpentine bands 208 and 206 of the stent 200 have a plurality of peaks 211 and troughs 209.

It is also noted that the proximal and distal ends of the inventive stents, as shown by way of example in FIGS. 5 and 6, for example, terminate with optional arcs 290 which are desirably of the same curvature as the leg portions 216*a,b* and 218*a,b* and the region therebetween of second serpentine band 206.

The number of serpentine segments and the number of wishbone connectors shown in the figures is illustrative only. Variant of the pictured stents may include additional or fewer serpentine segments and/or connecters as long as at least two serpentine bands are provided. The individual serpentine bands may also be provided with more or fewer peaks and troughs.

The use of wishbone connectors, as disclosed herein, is believed to result in increased flexibility due to the longer length of the connecter as compared with other connecters in many prior art stents. Although increasing the length of a connector may result in strut prolapse, many of the inventive designs disclosed herein may avoid the problem because the wishbone connectors have three distinct areas of different flexibility, with the elongate portion exhibit one degree of flexibility and the leg portions each exhibiting another degree of flexibility. Additional compression resistance is also gained because the wishbone connectors have increased mass of stent material as compared with non-wishbone longitudinal connectors. Moreover, because the wishbone connectors may provide increased flexibility, the serpentine segments may be made of thicker material to increase compression resistance of the stent.

Desirably, the inventive stents are made in balloon expandable form. It is also within the scope of the invention for the stents disclosed herein to be provided in self-expanding form or in hybrid form. Example of suitable materials for balloon and self-expanding stents are disclosed below.

In the above discussed embodiments, the inventive stents are of substantially uniform diameter. It is also within the scope of the invention to modify the stent patterns discussed above to prepare stents of non-constant diameter. For example, stent which taper in the expanded state may be made by decreasing the amplitude of the serpentine bands from one end of the stent to the other, or just along a desired portion of the stent. A tapered portion may be provided anywhere along the stent. For example, half of the stent, starting at one end of the stent, may be provided with a taper. Another way to achieve a tapered expanded stent is to change the stiffness of the serpentine bands and/or the wishbone connectors such that the stiffness of the serpentine bands and/or wishbone connectors varies along the length of the stent. The stiffness of the serpentine bands and/or wishbone connectors can be changed by altering length, width or thickness, adding additional stiffening material, using a chemical or mechanical means to alter the physical properties of the stent material, or applying one or a series of elastic elements about the stent.

Sections of different strength may also be provided in the inventive stents without creating a taper in the expanded state by varying the number of wishbone connectors between adjacent serpentine segments. For example, in one portion of the stent, more wishbone connectors may be provided between adjacent serpentine segments than in another portion of the stent. By having more wishbone connectors in one portion of the stent, that portion may be more flexible than portions having more wishbone connectors. In one embodiment, one or both ends of the stent may be more flexible than other portions of the stent. In another embodiment, one or both ends of the stent may be less flexible than other portions of the stent.

The inventive stent patterns disclosed herein may also be used in conjunction with other known stent designs to provide stents whose properties vary over the length or portions thereof.

The inventive stents disclosed here may be made of any suitable stent material. Examples of suitable stent material include metals such as gold, silver, platinum, stainless steel, elgiloy, MP35N, tantalum, titanium, shape-memory alloys such as nickel-titanium alloys referred to as Nitinol, as well as synthetic polymers and biological materials such as natural fibrin.

Such materials can be selected or coated to provide radio-opacity, if desired. For example, portions of the stent may be provided with radiopacity by providing those regions of the stent with a radiopaque coating such as, for example, gold.

The inventive stents disclosed herein may further comprise one or more therapeutic and/or polymeric coatings. The therapeutic coating may comprise one or more non-genetic therapeutic agents, genetic materials and cells and combinations thereof.

Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, antithrombin anticodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vasoactive mechanisms.

Genetic materials include anti-sense DNA and RNA, DNA coding for, anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor, cell cycle inhibitors including CD inhibitors, thymidine kinase ("TK") and other agents useful for interfering with cell proliferation the family of bone morphogenic proteins ("BMP's"),BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Desirable BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Cells can be of human origin (autologous or allogeneic) or from an animal source (xenogeneic), genetically engineered if desired to deliver proteins of interest at the transplant site. The cells may be provided in a deliveriny medial. The delivery media may be formulated as needed to maintain cell function and viability.

The inventive stents may further comprise a polymer coating in addition to or in place of the therapeutic coating. Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions, for example, BAYHDROL®, fibrin, collagen and derivatives thereof, polysaccharides such as celluloses, starches, dextrans, alginates and derivatives, hyaluronic acid, squalene emulsions. Polyacrylic acid, available as HYDROPLUS® (Boston Scientific Corporation, Natick, Mass.), and described in U.S. Pat. No. 5,091,205, the disclosure of which is hereby incorporated herein by reference, is particularly desirable. In a particular desirable embodiment of the invention, the polymer is a copolymer of polylactic acid and polycaprolactone.

In use, the stents disclosed herein are typically delivered via catheter to a desired bodily location. The choice of catheter will depend on the type of stent that is used. In the case of a balloon expandable stent, the stent may be expanded at the desired location by inflating a medical balloon disposed within the stent. In the case of a self-expanding stent, the stent is allowed to self-expand by withdrawing a sheath disposed about the stent or by increasing the stent temperature or through any other known methods of causing a stent to self-expand. The choice of catheter will also depend on the location to which the stent is delivered.

The inventive stents may be used in arteries and vessels including coronary vasculature, the esophagus, the trachea, the colon, the biliary tract, the urinary tract, the prostate, the brain, urethras, fallopian tubes, and bronchial tubes as well as in any other suitable body vessel.

Any suitable method may be used to manufacture the inventive stents. For example, the inventive stents may be made by removing material from a tube via chemical etching, laser etching or any other suitable materials removal process. The inventive stents may also be manufactured by removing material from a sheet and then rolling the sheet. Optionally, two opposing edges of the sheet may be secure one to the other to prevent the sheet from unrolling. The inventive stents may also be manufactured by preparing individual portions of the stent and connecting them to one another via welding, the use of adhesives or any other suitable joining technique. This list of manufacturing techniques is not meant to be exhaustive. Other manufacturing techniques may also be used to manufacture the inventive stents.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

The particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 4 may be taken as alternatively dependent on claim 2, or on claim 3; claim 5 may be taken as alternatively dependent from any of claims 1-3, etc.).

This completes the description of the preferred and alternate embodiments of the invention. Those skilled in the art may recognize other equivalents to the specific embodiment described herein which equivalents are intended to be encompassed by the claims attached hereto.

We claim:

1. A stent having a proximal end and a distal end, the stent comprising:
    a plurality of axially spaced serpentine bands, each serpentine band having a proximal and distal end and consisting of a plurality of interconnected struts, the struts of substantially the same length, serpentine bands which are adjacent one another connected one to the other; and
    a plurality of wishbone connectors, each wishbone connector connecting two serpentine bands which are adjacent one another and having an elongate portion which is disposed between the two serpentine bands and does not overlap longitudinally with either of the two serpentine bands, the elongate portion having a proximal end and a distal end, the proximal end having two legs extending therefrom to one of the two serpentine bands and the distal end having two legs extending therefrom to the other of the two serpentine bands, the two legs extending from the proximal end of the elongate portion of each wishbone connector being circumferentially and longitudinally displaced from the two legs extending from the distal end of the elongate portion of the wishbone connector,
    at least one wishbone connector connecting serpentine bands which are adjacent one another.

2. The stent of claim 1 wherein at least two wishbone connectors extend between each two adjacent serpentine bands.

3. The stent of claim 2 wherein each serpentine band comprises a plurality of alternating peaks and troughs and each leg of each wishbone connector extends from a location on a serpentine band between a peak and a trough.

4. The stent of claim 1 wherein the elongate portions of the connectors extend in a direction non-parallel to the longitudinal axis of the stent.

5. The stent of claim 4 wherein the elongate portions of the connectors have a plurality of turns.

6. The stent of claim 1 wherein each serpentine band comprises a plurality of alternating peaks and troughs and each leg of each wishbone connector extends from a location on a serpentine band between a peak and a trough.

7. The stent of claim 1 wherein each serpentine band comprises alternating peaks and troughs, the number of peaks in the stent being twice the number of wishbone connectors.

8. The stent of claim 1 wherein the width of the serpentine bands exceeds the width of the wishbone connectors.

9. A stent having a first proximal end and a distal end, the stent comprising:
    a plurality of axially spaced serpentine bands, each serpentine band having a proximal end and a distal end, each serpentine band having a plurality of peaks and troughs, all of the peaks longitudinally aligned with one another, all of the troughs longitudinally aligned with one another, serpentine bands which are adjacent one another connected one to the other; and
    a plurality of wishbone connectors, each wishbone connector connecting two serpentine bands which are adjacent one another and having an elongate portion which is disposed between the two serpentine bands and does not overlap longitudinally with either of the two serpentine bands, the elongate portion having a proximal end and a distal end, the proximal end having two legs extending therefrom to one of the two serpentine bands and the distal end having two legs extending therefrom to the other of the two serpentine bands, the two legs extending from the proximal end of the elongate portion of each wishbone connector being circumferentially and longitudinally displaced from the two legs extending from the distal end of the elongate portion of the wishbone connector,
    at least one wishbone connector connecting serpentine bands which are adjacent one another.

10. The stent of claim 9 wherein at least two wishbone connectors extend between each two adjacent serpentine bands.

11. The stent of claim 10 wherein each serpentine band comprises a plurality of alternating peaks and troughs and each leg of each wishbone connector extends from a location on a serpentine band between a peak and a trough.

12. The stent of claim 9 wherein the elongate portions of the connectors extend in a direction non-parallel to the longitudinal axis of the stent.

13. The stent of claim 12 wherein the elongate portions of the connectors have a plurality of turns.

14. The stent of claim 9 wherein each serpentine band comprises a plurality of alternating peaks and troughs and each leg of each wishbone connector extends from a location on a serpentine band between a peak and a trough.

15. The stent of claim 9 wherein each serpentine band comprises alternating peaks and troughs, the number of peaks in the stent being twice the number of wishbone connectors.

16. A stent comprising a plurality of first and second alternating serpentine bands, the first serpentine bands being of one geometry and the second serpentine bands being of a geometry different than the first serpentine bands, each of the first and second serpentine bands having a proximal end and a distal end, each second serpentine band connected to one proximally adjacent first serpentine band via a plurality of first connectors and to one distally adjacent first serpentine band via a plurality of second connectors, each second serpentine band being characterized by a repeating pattern of two or more consecutive first connectors extending distally from the second serpentine band followed by two or more second connectors extending proximally from the second serpentine band, the two or more first connectors being circumferentially and longitudinally offset from the two or more second connectors.

17. The stent of claim 16 wherein the first serpentine bands are comprised of a plurality of interconnected first struts, the second serpentine bands are comprised of a plurality of interconnected second struts, the second struts being narrower than the first struts.

18. The stent of claim 16 wherein at least some of the second serpentine bands each comprise a plurality of openings of a first shape and a plurality of openings of a second shape, the second shape different from the first shape.

19. The stent of claim 16 wherein at least some of the second serpentine bands each comprise a plurality of openings some of which are non-parallel to the longitudinal axis of the second serpentine segment.

20. The stent of claim 16 wherein the first and second connectors are substantially straight.

\* \* \* \* \*